United States Patent [19]

Hill et al.

[11] 4,452,994

[45] Jun. 5, 1984

[54] PROCESS FOR ISOLATING ORGANIC COMPOUNDS AND LITHIUM SALT COMPLEXES USEFUL IN SAID PROCESS

[75] Inventors: John B. Hill, Woodstock; Robert A. Erickson, Des Plaines, both of Ill.

[73] Assignee: G. D. Searle & Co., Skokie, Ill.

[21] Appl. No.: 239,822

[22] Filed: Mar. 2, 1981

[51] Int. Cl.$^3$ ............................................. C07C 177/00
[52] U.S. Cl. ................................. 560/121; 260/239.57; 260/397.25; 260/397.3; 260/397.4; 548/339; 548/545; 562/463; 562/464; 562/494; 562/503; 564/216; 564/437; 568/27; 568/376; 568/442; 568/742
[58] Field of Search ......................... 560/121; 562/503

[56] References Cited

U.S. PATENT DOCUMENTS 3,755,447  8/1973  Klemann et al. .................. 260/563
3,981,929  9/1976  Davis et al. ........................ 568/750

OTHER PUBLICATIONS

Johnson et al., J. Am. Chem. Soc., 99, 7738 (1977).

Primary Examiner—Robert Gerstl
Attorney, Agent, or Firm—John J. McDonnell

[57] ABSTRACT

An improved process for isolating organic compounds from crude product or reaction mixtures by dissolving said crude product or reaction mixture in a suitable solvent, contacting the resulting solution with a lithium salt to form a solid metal salt complex, separating, and thereafter recovering a pure product by decomposing the lithium salt complex.

7 Claims, No Drawings

PROCESS FOR ISOLATING ORGANIC COMPOUNDS AND LITHIUM SALT COMPLEXES USEFUL IN SAID PROCESS

BACKGROUND OF THE INVENTION

The formation of alcoholates of anhydrous metal halides has been documented in the literature, and the separation of organic mixtures by formation of metal complexes has been reported. See Sharpless et al, J. Org. Chem., Vol. 40, No. 9, pp 1252-1257(1975). Sharpless et al teach the use of divalent metal salts, particularly the salts of calcium and manganese in the resolution of alcohol mixtures by preferential complexation by calcium chloride or manganese chloride with one alcohol of the mixture, using catalytic amounts of ethanol to enhance the complexing ability of metal halides. The Sharpless et al resolutions are restricted to simple alcohols.

Weber et al. U.S. Pat. No. 4,057,541 disclose a process for isolating 3-hydroxy steroids and 3-keto steroids from mixtures thereof by dissolving the mixtures in an organic solvent, mixing the dissolved mixture with calcium bromide to form insoluble adducts of the steroids, separating the insoluble adducts and splitting the adducts to regenerate the free steroid. Methyl isobutyl ketone and/or methyl n-amyl ketone is used as the solvent.

Weber et al. specifically teach away from the use of metal salts other than calcium bromide (in its hydrate form) stating at Column 2, lines 32-34 "The use of other metal salts which are otherwise suitable for adduct formation also leads to poorer results as compared to the method of the present invention."

It has now been found that a number of organic compounds, particularly pharmaceutical compounds with complex structures i.e., prostaglandins, steroids, antibiotics, etc., which are generally difficult to isolate and purify, are readily and advantageously isolated and purified by the use of complexation of the crude product or reaction mixture with a lithium salt selected from the group consisting of lithium bromide, lithium iodide, lithium perchlorate, and lithium fluoroborate in the presence of a suitable solvent.

SUMMARY

The process of the present invention generally comprises forming a lithium salt complex with a crude reaction mixture in the presence of a suitable solvent, and recovering the pure product therefrom by decomposition.

DETAILED DESCRIPTION OF PREFERRED EMBODIMENTS

In the practice of the present invention, the crude reaction mixture, which may contain the crude product or a mixture of crude products, is contacted or dissolved in any suitable non-hydroxylic organic solvent, and from about 1.0 to about 10 moles of a lithium salt per mole of product is added thereto. It is preferred to add from about 2 to about 5 moles of lithium salt per mole of substrate to be complexed. More preferably, in specific embodiments of the present invention, prostaglandins may be complexed with about 2 to about 5 moles of lithium salt; steroids may be complexed with about 1.5 to 3 moles of lithium salt; and metronidazole may be complexed with about 1 to 2 moles of lithium salt per mole of substrate.

A lithium salt is preferably selected from the group consisting of lithium bromide, lithium iodide, lithium perchlorate, and lithium fluoroborate.

The solvent can be any non-hydroxylic organic solvent such as toluene, methylene chloride, hexane, etc., and the selection of solvent is primarily dependent upon the nature of the compound to be isolated. In the case of steroids, methylene chloride, toluene and ether are the preferred solvents. In the case of prostaglandins, the preferred solvents are toluene, hexane and methylene chloride. Ethers, hydrocarbons, halocarbons, etc., are also readily employed in the practice of this invention depending upon the substrate.

The complexation reaction is run for an effective amount of time and at an effective temperature to complete the reaction. Commonly, temperatures of from about 0° to about 100° C., preferably from about 20° to 30° C. for from about 15 minutes to about 48 hours, preferably for from about 2 to about 18 hours, are utilized.

The addition of a small amount of water or a lower alcohol, i.e. a $C_1-C_3$ alcohol (methanol, ethanol, propanol, or 2-propanol) as a catalyst has been found to be advantageous.

In order to cleave the lithium salt complex and obtain the pure product, the complex is separated and placed in a large excess (about 10 to about 100 moles) of water or a lower alcohol i.e., $C_1-C_3$ alcohol, and allowed to decompose for an effective amount of time and at an effective temperature to complete the reaction. The time and temperature commonly utilized for cleaving the lithium salt complex are from 5 minutes to 24 hours at temperatures of from about 0° C. to about 100° C., preferably about 10° to about 35° C. for from 5 minutes to about 24 hours. Any common organic solvent can be added if desired, but the presence of solvent is not necessary.

The time and temperature for the cleavage step depend upon the nature of the compounds being isolated. In the case of prostaglandins, temperatures of from 0° to 10° C. are preferred and the reaction time ranges from about 5 minutes to about 2 hours. Steroids generally require from 20 minutes to 3 hours, while metronidazole requires a 24 hour cleavage period. In some instances, it is advantageous to boil the reaction mixture to speed up the cleavage.

It has been found that certain lithium salts exhibit selectivity toward various functional groups and the choice of the particular lithium salt depends upon the nature of the substrate. For example, lithium bromide advantageously complexes alcohols, phenols, amides, imides, carboxylic acids primary or secondary amines having a $K_b$ (dissociation constant in water at 25° C.) of at least $10^{-10}$ and sulfoxides. Lithium perchlorate advantageously complexes all of the above plus ketones and aldehydes. Thus, the choice of the particular lithium salt is dependent on the particular substrate.

The method of the present invention has wide applicability to a number of organic compounds which are advantageously isolated and/or purified by the use of a lithium salt. For example, analgesic agents such as acetominophen and mefenamic acid; anti-inflammatory agents such as indomethicin and phenlbutazone; beta-blockers such as isoproteranol and propanolol; antibiotics such as penicillin G, ampicillin, amoxicillin, cephalosporins, chloramphenicol, erythromycin, tetracycline and sulfachlorpyridizines; anti-protozoal agents such as metronidazole; antimetazoal agents such as hycanthone and mebendazole; vitamins such as vitamins A, D, E, biotin and folic acid; prostaglandins; H₂ receptor antagonists such as cimetidine; progestins such as norgestrel and norethindrone; tranquilizers such as diazepam and chlordiazepoxide; diuretics such as furosemide; antihypertensive agents such as spironolactone, clonidine and propranolol hydrochloride; corticosteriods such as cortisol and dexamethasone; and antiarrhythmic agents such as disopyramide phosphate.

The present invention also provides intermediates or metal salt complexes of organic compounds, having the formula R.(Li X)$_m$(H$_2$O)$_n$ wherein R is an organic compound to be isolated; X is an anion selected from the group consisting of bromide, iodide, perchlorate, and flouroborate; m is a number from 1 to 10 and n is a number from 0 to 10.

The present invention has been found to be particularly advantageous in isolating prostaglandins and steroids. By using the present lithium salt complex process in the isolation of prostaglandins, over 70% of the undesired reaction products, which are normally separated by chromatography, are eliminated and the amount of chromatography is reduced by about 60%.

The isolation of steroids is also greatly facilitated by the present process, and in the case of methyl testosterone, the present process provides an excellent way of isolating the steroid from the reaction mixture. In all cases, yields are increased.

The invention will appear more fully from he examples which follow. These examples are given by way of illustration only and are not to be construed as limiting the invention either in spirit or scope as many modifications both in materials and in methods will be apparent from the disclosure to those skilled in the art.

EXAMPLE 1

Preparation and isolation of (±)-methyl 11α,16-dihydroxy-16-methyl-9-oxoprost-13E-en-1-oate To a mixture of 40 ml tetrahydrofuran (THF) and 40 ml water is added 68.8 g of crude (±)-methyl 16-methyl-9-oxo-11α-[(triethylsilyl)oxy]-16-[(trimethylsilyl)oxy]-prost-13E-en-1-oate (containing 26.3 g maximum of pure compound) and 120 ml of acetic acid. The mixture is stirred under nitrogen for 1-2 hours. The resulting mixture is diluted with 300 ml of water and 300 ml of ether. The ether layer is separated and washed with 150 ml of water, 500 ml of saturated aqueous sodium bicarbonate and twice with saturated aqueous sodium chloride. All of the ether extracts are combined and dried over sodium carbonate, filtered and evaporated to dryness 'in vacuo' to give 67.5 g of an oil containing (±)-methyl 11α,16-dihydroxy-16-methyl-9-oxoprost-13E-3en-1-oate.

The crude oil obtained above is dissolved in 250 ml toluene and added over a 30 second period to a vigorously stirred suspension of 135 g lithium bromide in 500 ml of toluene. After 30 minutes, the solid complex is removed by filtration, washed with 500 ml of toluene, and pulled dry on the filter under nitrogen.

Analysis: C, 6.46 H, 1.91 Br, 73.11, H$_2$O, 7.89.

DSC: Endotherms at 43 (sharp), 77 (broad, shallow), 162 (sharp) and 251° C. (sharp).

DSC refers to a method of analysis described in Differential Scanning Colorimetry by J. L. McNaughton and C. T. Mortimer; Perkin & Elmer, 1975. The apparatus used for evaluation is a DuPont model 900.

The complex is dissolved in 400 ml of ethyl acetate with external cooling. One liter of water is added and the mixture stirred briefly. The ethyl acetate layer is separated and washed with 100 ml of water and 100 ml saturated aqueous sodium chloride. After filtration through Celite, manufactured by Johns Mansville Co., the solvent is evaporated 'in vacuo.' The residual oil weighed 16.4 g (88% of Theory) and contained only (±)-methyl 11α,16-dihydroxy-16-methyl-9-oxoprost-13E-en-1-oate and small amounts of other prostaglandins.

EXAMPLE 2

Preparation and isolation of (±)-methyl 11α,16-dihydroxy-16-methyl-9-oxoprost-4Z,13E-dien-1-oate To a mixture of 250 ml water and 750 ml acetic acid is added 124.92 grams of crude (±)-methyl 16-methyl-9-oxo-11α-[(triethylsilyl)oxy]-16-[(trimethylsilyl)oxy]-prost-4Z,13E-dien-1-oate (containing 24 g maximum of pure compound) and stirred under argon for 2 hrs. The resulting mixture is diluted with 1.0 liter of water and 1.0 liter of ether. The ether layer is separated and washed with 600 ml of water (twice), 800 ml of 5% aqueous sodium bicarbonate, 300 ml of 5% aqueous sodium bicarbonate (twice), and 100 ml of saturated aqueous sodium chloride. The aqueous extracts are combined and extracted with 200 ml of ether (twice). The ether extracts are combined and washed with 250 ml of 5% aqueous sodium bicarbonate (5 times) and 100 ml of saturated aqueous sodium chloride. The resultant ether solution is dried over sodium sulfate, filtered through Celite, and evaporated to dryness 'in vacuo' to give 119 g of an oil containing (±)-methyl 11α,16-dihydroxy-16-methyl-9-oxoprost-4Z,13E-dien-1-oate.

The crude oil obtained above is dissolved in 458 ml of ether and 229 ml of hexane and added rapidly (about 1 min) to a stirred suspension containing 228.88 g of lithium bromide in 915 ml of ether and 457 ml of hexane. The solid complex is removed by filtration and washed with 1750 ml of 2:1 ether:hexane. The complex is added to a stirred mixture containing 1.0 liter of ethyl acetate and 1.0 liter of water. After 30 minutes, the ethyl acetate layer is separated, dried over sodium sulfate, filtered through Celite, and evaporated in 'in vacuo'. The residual oil weighed 21.35 g (89% of Theory) and contained (±)-methyl 11α,16-dihydroxy-16-methyl-9-oxoprost-4Z,13E-dien-1-oate and only small amounts of impurities.

EXAMPLE 3

Preparation and isolation of 17α-methyltestosterone

To 106 ml THF is added 16.0 g of androst-4-ene-3,17-dione-3-ethyl enol ether and the mixture is treated with 55.0 ml of a (1.4M) methyllithium/ether solution at 5° C. The product is extracted with methylene chloride after treatment with water and phosphoric acid. The extracts are dried over sodium sulfate and evaporated to dryness 'in vacuo' to yield 15.6 g yellow solids.

The crude reaction products are dissolved in 140 ml toluene, 65 ml methylene chloride and 25 ml ether. While stirring vigorously, 2.0 ml water, followed by 8.9 g of lithium bromide are added and the mixture stirred for two hours at 24° C.

The resultant slurry is filtered and washed with 2×50 ml cold wash solution (4:1, hexane:methylene chloride). Solids are dried in a vacuum oven at 24° C. to yield 19.98 g of the 17α-methyltestosterone/lithium bromide complex.

Analysis: C,31.56; H,5.72; Br,34.55; $H_2O$, 19.30.
m.p. 150°–154.5° C.

The complex is decomposed by treating 5.0 g with 120 ml water and 5 ml acetone and stirring the mixture for 20 minutes. The freed product is filtered and washed with 2×20 ml water, then dried to yield 1.85 g of 17α-methyltestosterone (which when projected for the whole sample gives an overall 55.8% recovery).

EXAMPLE 4

'In situ' isolation of 17α-methylestosterone

In a dry flask under an inert atmosphere, 16.0 g of androst-4-ene-3,17-dione-3-ethyl enol ether in 140 dry toluene is treated with 48.0 ml of a (1.4M) methyl lithium/ether (containing LiBr) solution at 0° C. After stirring for 1 hr., the reaction is treated with water and phosphoric acid and the resulting slurry diluted with 65 ml methylene chloride. After stirring vigorously for 60 minutes, the tan solids are filtered and washed with 2×125 ml cold wash solution (4:1 hexane:methylene chloride). The solids are dried 'in vacuo' to yield 29.73 g of 17α-methyltestosterone/lithium bromide complex.

The complex is decomposed by treating 5.0 g with 120 ml water and 5 ml acetone and stirring the mixture for 20 minutes. The freed product is filtered and washed with 2×20 ml water, then dried to yield 2.30 g of 17α-methyltestosterone (which when projected for the whole sample gives an overall 88.8% yield).

EXAMPLE 5

Isolation of 17α-Methyltestosterone

A mixture containing 13.1 g of methyltestosterone and 2.2 g of androstenedione is dissolved in 140 ml toluene, 65 ml of methylene chloride, 25 ml of ether and 3.0 ml of water. 6.2 grams of lithium bromide is added and the mixture is stirred vigorously for 16 hrs. The resultant mixture is filtered and the solids washed with a cold 4:1 solution of hexane and methylene chloride. The product is dried 'in vacuo' to give 21.05 g of the 17α-methyl testosterone/LiBr complex.

Analysis: C,45.59; H,7.02; Br,24.94; $H_2O$, 15.28,
m.p. 156°–159° C.

The complex is hydrolyzed by treating 5.0 g with 120 ml water and 5 ml acetone and stirring for 20 minutes. The resultant precipitate is filtered, washed with water and dried to yield 2.76 g of pure 17α-methyltestosterone (which when projected for the whole sample gives an 88.7% yield).

EXAMPLE 6

Preparation and isolation of 6β,17-dihyroxy-3-oxo-17-preg-4-ene-7α,21-dicarboxylic acid-7-isopropyl ester-γ-lactone To 80 ml isopropyl alcohol is added 15.5 g of 17-hydroxy-3-oxo-17α-preg-4-ene-7α,21-dicarboxylic acid-7-isopropylester-lactone and the mixture is treated with 0.68 g tosic acid and 15.9 ml of triethyl orthoformate at 24° C. The reaction is complete after 30 minutes. Pyridine is added, the reaction stirring for 15 minutes, and the solvents are evaporated 'in vacuo' at 40° C.

The residue is dissolved in 100 ml dry THF and the turbid solution is cooled to 0°±10° C. To this solution is added a mixture containing 17.5 ml of 40% peracetic acid, 0.80 g of sodium acetate and 11.6 ml of water over 30 minutes. The reaction is stirred for an additional 30 minutes at 0°±10° C., then let stand overnight.

The reaction is diluted with 200 ml of water and extracted with 2×108.9 ml of a solution containing 99 ml ethyl acetate and 9.9 ml hexanes. The organics are washed with 3×140 ml of water, 115 ml of 5% sodium bicarbonate, 56 ml of 5% sodium sulfite and water, then dried over sodium sulfate. The solvents are evaporated in 'in vacuo' to give a yellow oil.

The resultant oil is dissolved in 145 ml toluene and 26 ml ether and treated with 2.0 ml water and 7.1 g lithium bromide. The mixture is stirred vigorously for 2 hours. The solids are filtered and washed with 2×50 ml of cold wash solution (4:1, hexane:methylene chloride). The filter cake is dried 'in vacuo' overnight to yield 17.6 g of off-white solid complex.

Analysis: C,35.94; H,4.67; Br,34.82; $H_2O$, 14.32;
m.p. 175°–178° C.

The complex is hydrolyzed by treating 5.0 g with 120 ml water and 5 ml acetone and stirring the mixture for 20 minutes. The freed product is filtered and washed with 2×20 ml of water, then dried overnight to yield 2.37 g of 6β,17-dihydroxy-3-oxo-17α-preg-4-ene-7α,21-dicarboxylic acid 7-isopropyl ester-γ-lactone.

EXAMPLE 7

Preparation of metronidazole/lithium bromide complex

To a solution containing 2.18 g of metronidazole in 150 ml chloroform is added 11.0 g lithium bromide and the resulting mixture is stirred for 18 hours under argon. The white solids are removed by filtration and washed with 100 ml cold chloroform, then dried in 'in vacuo' for 20 hours to yield 12.09 g of white, solid, metronidazole/lithium bromide complex.

Analysis: C, 7.45; H, 1.61; N, 4.18; Br, 72.04; $H_2O$, 4.33; m.p.: softens at 147° C.

EXAMPLE 8

Isolation of 11α-hydroxyandrostene-3,17-dione

To a solution of 28.1 ml methylene chloride, 7.8 ml hexane and 0.2 ml water is added 1.52 g of a fermentation mixture with a sterol content of 30–60% (consisting of androstenedione and 11α-hydroxy androstenedione). To the resulting solution 1.34 g of lithium bromide is added and the mixture stirred overnight at ambient temperatures. The resultant mixture is filtered, the solids washed with a 3.5:1, hexane methylene chloride solution and dried 'in vacuo.'

The yield of 11α-hydroxyandostenedione/LiBr complex is 1.95 g.

Analysis: C, 15.65; H, 4.42; Br, 61.40; $H_2O$, 15.42. DSC: Endotherms at 45° (sharp), 219° (sharp) and 278° C. (sharp).

The complex is hydrolyzed by treating with 60 ml water and 2.5 ml acetone with stirring for 20 minutes. The freed product is filtered and washed with 2×10 ml of water, then dried in 'in vacuo' to give 0.91 g of 11α-hydroxy androstene-3,17-dione.

EXAMPLE 9

Isolation of β-naphthol

To a solution containing 140 ml of toluene, 25 ml of ether and 7.35 g of β-naphthol is added 1.0 ml of water, followed by 8.86 g of lithium bromide. The mixture is stirred for 18 hrs. The solids are removed by filtration, washed with 50 ml of cold 4:1, hexane:methylene chloride and dried 'in vacuo' to give 15.58 g of β-naphthol/-lithium bromide complex.

Analysis: C, 30.14; H, 5.61; Br, 50.42; $H_2O$, 8.31.
DSC: Endotherms at 48 (sharp), 153 (broad, shallow), 162 (broad), 283° C. (sharp).

A mixture of 200 ml water and 14.6 g of the complex is stirred for 2 hrs, filtered, washed with 100 ml of water and air dried to give 4.8 g of β-naphthol (72% overall recovery when projected for entire sample).

EXAMPLE 10

Isolation of 1-aminoindan

To a solution containing 140 ml toluene, 25 ml ether and 6.8 g of 1-aminoindan is added 8.86 g of lithium bromide. The mixture is stirred for 18 hrs. The solids are removed by filtration, washed 2 times with 50 ml of cold 4:1, hexane:methylene chloride, and dried 'in vacuo' to give 14.09 g of 1-aminoindan/lithium bromide complex.

Analysis: C, 30,73; H, 4.77; N, 4.10; Br, 45.98; $H_2O$, 7.24.
DSC: Endotherms at 46 (sharp), 79 (sharp), 92 (sharp), 210° C. (sharp).

A mixture of 200 ml water and 13.5 g of the complex is stirred with 100 ml of ether for 2 hrs. The ether layer is separated, dried ($Na_2SO_4$) and evaporated 'in vacuo' to give 4.7 g of 1-aminoindan (72% overall recovery when projected for the entire sample).

EXAMPLE 11

Isolation of N-(1-adamantyl)-acetamide

To a solution containing 140 ml toluene 65 ml methylene chloride, 25 ml ether and 9.84 g of N-(1-adamantyl)-acetamide is added 2.0 ml of water and 18.5 g of lithium perchlorate. The mixture is stirred for 18 hrs. The solids are removed by filtration, washed with 50 ml of cold 4:1, hexane:methylene chloride, and dried 'in vacuo' to yield 30.53 g of N-(1-adamantyl)-acetamide/-lithium perchlorate complex.

Analysis: C, 22.62; H, 4.93; N, 2.34, Cl, 17.66; IR(KBr): 1660 $cm^{-1}$.
DSC: Endotherm at 93° C. (sharp), Exotherm at 345° C. (sharp).

A portion of the complex weighing 24.12 g is hydrolyzed as in Example 9 to give 6.69 g N-(1-adamantyl)-acetamide (86% overall recovery when projected for the entire sample).

EXAMPLE 12

Isolation of diphenyl sulfoxide

To a solution containing 140 ml toluene, 65 ml methylene chloride, 25 ml ether and 14.3 g of diphenyl sulfoxide is added 2.0 ml of water and 18.5 g of lithium perchlorate. The mixture is stirred for 18 hrs. The solids are removed by filtration, washed with 50 ml of cold 4:1, hexane:methylene chloride, and dried 'in vacuo' to give 30.49 g of diphenyl sulfoxide/lithium perchlorate complex.

IR(KBr): 1640 $cm^{-1}$.
DSC: Endotherm at 95° C. (sharp).
Exotherms at 335 (broad) and 349° C. (sharp).

A portion of the complex weighing 29.36 g is hydrolyzed as in Example 9 to give 7.46 g of diphenyl sulfoxide (54% overall recovery when projected for the entire sample).

EXAMPLE 13

Isolation of 3,4dibenzyloxy benzaldehyde

To a solution containing 140 ml toluene, 65 ml methylene chloride, 25 ml ether and 16.2 g of 3,4-dibenzyloxybenzaldehyde is added 2.0 ml of water and 18.5 g of lithium perchlorate. The mixture is stirred for 18 hrs. The solids are removed by filtration, washed with 50 ml of cold 4:1, hexane:methylene chloride and dried 'in vacuo' to yield 26.85 g of 3,4-dibenzyloxybenzaldehyde/lithium perchlorate complex.

Analysis: C, 21,96; H, 3.14;
DSC: Endotherms at 88 (sharp, weak), 94° C. (sharp). Exotherm at 332° C. (broad).

A portion of the complex weighing 25 g is hydrolyzed as in Example 9 to give 4.98 g of 3,4-dibenzyloxybenzaldehyde (33% overall recovery when projected for the entire sample).

EXAMPLE 14

Preparation of 1,3-cyclohexanedione/lithium bromide complex

To a solution containing 140 ml of toluene, 65 ml methyl chloride, 25 ml ether and 5.72 g of 1,3-cyclohexane-dione is added 2.0 ml of water and 8.86 g of lithium bromide. The mixture is stirred for 18 hrs. The solids are removed by filtration, washed with 100 ml of cold 4:1, hexane:methylene chloride and dried 'in vacuo' to give 16.58 g of 1,3-cyclohexanedione/lithium bromide complex.

Analysis: C, 21,55; H, 3.77.
DSC: Endotherms at 102 (sharp), 118 (sharp), 140 (sharp), 176 (sharp), 211 (broad), 265° C. (broad). Exotherm at 225° C. (broad).

EXAMPLE 15

Preparation of succinimide/lithium perchlorate complex

To a solution containing 420 ml toluene, 195 ml methylene chloride, 75 ml ether and 5.15 g of succinimide is added 2.0 ml of water and 18.5 g of lithium perchlorate. The mixture is stirred for 18 hrs. The solids are removed by filtration, washed 2 times with 50 ml of cold 4:1, hexane:methylene chloride, and dried 'in vacuo' to give 24.18 g of succinimide/lithium perchlorate complex.

DSC: Endotherm at 93° (sharp),
Exotherm at 307° (broad),
IR (KBR): 1695 $cm^{-1}$

EXAMPLE 16

Preparation of benzoic acid/lithium bromide complex

To a solution containing 2.49 g of benzoic acid, 85 ml hexane and 15 ml methylene choride is added 3.54 lithium bromide and the resulting mixture is stirred for two hours under argon. The solids are removed by filtration and washed wtih 2×20 ml cold wash solution (85:15, hexane:methylene chloride), then dried 'in vacuo' for three hours to yield 5.7 g of benzoic acid/lithium bromide complex.

C, 22.43; H, 2.72; Br, 53.00; $H_2O$,-3.56

DSC: Endotherms at 90, 106, 162, 228, 245 & 263° C.

EXAMPLE 17

Preparation of testosterone/lithium fluoroborate complex

To a solution containing 14.7 g of testosterone in 140 ml of toluene, 65 ml of methylene chloride, 25 ml of ether and 2.0 ml of water is added 9.6 g of lithium fluoroborate and the resulting mixture is stirred for 2 hours. The solids are removed by filtration and washed with 2×50 ml cold wash solution (4:1, hexane:methylene chloride). The solids are dried 'in vacuo' for 16 hours to yield 12.99 g of testosterone/lithium fluoroborate complex.

Analysis: C, 13.42; H, 3.12; F, 49.39; $H_2O$, 12.49;
DSC: Endotherms at 117 (sharp), 225 (broad), 333° C. (sharp)

EXAMPLE 18

Preparation of testosterone/lithium iodide complex

To a solution containing 14.7 g of testosterone in 140 ml of toluene, 65 ml methylene chloride, 25 ml of ether and 2.0 ml of water is added 13.65 g of lithium iodide and the resulting mixture is stirred for 2 hours. To aid in filtration of the mixture 160 ml toluene and 50 ml ether is added. The solids are removed by filtration and washed with 2×50 ml of cold wash solution (4:1, hexane:methylene chloride) followed by 100 ml of hexane. The solids are dried 'in vacuo' for 16 hours, then under high vacuum for 24 hours to yield 31.73 g of testosterone lithium iodide complex.

Analysis: C, 40.07; H, 6.17; I,38.04; $H_2O$, 9.76;
DSC: Endotherms at 228° and 234° C.
Exotherm at 355° C.

EXAMPLE 19

Preparation of androstenedione/lithium perchlorate complex

To a solution containing 1.46 g of androstenedione, 14.0 ml toluene, 6.5 ml methylene chloride, 2.5 ml ether and 0.2 ml water is added 1.85 g lithium perchlorate and the resulting mixture is stirred vigorously for 75 minutes under argon. The solids are removed by filtration and washed with 2×5 ml of hexane and dried 'in vacuo' to yield 3.42 g, androstenedione/lithium perchlorate complex.

C, 31.85; H, 4.20 Cl, 19.37; $H_2O$ 5.63;

EXAMPLE 20

Substitution of an equivalent quantity of 11β,15-dihydroxy-15,20-dimethyl-9-oxoprost-13E-en-1-oic acid in the procedure of Example 1 affords the corresponding lithium bromide complex that is hydrolyzed to yield a pure product.

EXAMPLE 21

Substitution of an equivalent quantity of methyl 3-hydroxy-5-oxo-1-cyclopentene-1-heptanoate in the procedure of Example 1 affords the corresponding lithium bromide complex that is hydrolyzed to yield a pure product.

EXAMPLE 22

Substitution of an equivalent quantity of (±) 1,11,16-trihydroxy-16-methyl-prost-13E-en-9-one in the procedure of Example 1 affords the corresponding lithium bromide complex that is hydrolyzed to yield a pure product.

EXAMPLE 23

Substitution of an equivalent quantity of (±) 11,16-dihydroxy-1-(hydroxymethy)-16-methylprost-13E-ene-1,9-dione in the procedure of Example 1 affords the corresponding lithium bromide complex that is hydrolyzed to yield a pure product.

EXAMPLE 24

Substitution of an equivalent amount of 11α,15S-dihydroxy-15-methyl-9-oxo-prost-13E-en-1-oic acid in the procedure of Example 1 affords the corresponding lithium bromide complex that is hydrolyzed to yield a pure product.

EXAMPLE 25

Substitution of an equivalent amount of 11,α,15S-dihydroxy-15-methyl-9-oxoprosta-5Z,13E-dien-1-oic acid in the procedure of Example 1 affords the corresponding lithium bromide complex that is hydrolyzed to yield a pure product.

EXAMPLE 26

Substitution of an equivalent amount of 11α,15S-dihydroxy-16,16-dimethyl-9-oxoprosta-5Z,13E-dien-1-oic acid in the procecure of Example 1 affords the corresponding lithium bromide complex that is hydrolyzed to yield a pure product.

EXAMPLE 27

Substitution of an equivalent amount of 11,15-dihydroxy-11,16,16-trimethyl-9-oxoprosta-5,13-dien-1-oic acid in the procedure of Example 1 affords the corresponding lithium bromide complex that is hydrolyzed to yield a pure product.

EXAMPLE 28

Substitution of an equivalent amount of methyl 7-[3,5-dihydroxy-2-(3-hydroxy-4-phenoxy-1-butenyl)cyclopentyl]-5-heptenoate in the procedure of Example 1 affords the corresponding lithium bromide complex that is hydrolyzed to yield a pure product.

EXAMPLE 29

Substitution of an equivalent amount of 3-[[3α-hydroxy-2-(3-hydroxy-1-octenyl)-5-oxocyclopentyl]methyl]phenoxyacetic acid in the procedure of Example 1 affords the corresponding lithium bromide complex that is hydrolyzed to yield a pure product.

EXAMPLE 30

Substitution of an equivalent amount of 7-[2-[4-(-3-chlorophenoxy)-3-hydroxy-1-butenyl]-3,5-dihydroxycyclopentyl]-4,5-heptadienoic acid in the procedure of Example 1 affords the corresponding lithium bromide complex that is hydrolyzed to yield a pure product.

What is claimed is:

1. The process for isolating an 11,16 or 11,15 dihydroxy prostaglandin from a reaction mixture or crude mixture containing such dihydroxy prostaglandin which comprises dissolving said reaction mixture or crude mixture in a non-hydroxylic organic solvent, contacting the resultant solution with a lithium salt selected from the group comprising lithium bromide, lithium iodide, lithium perchlorate, and lithium fluoroborate in a concentration from about 1 mole to about 10 moles of said lithium salt per mole of product to form a solid complex, separating the complex, and decomposing the complex to recover purified dihydroxy prostaglandin.

2. The process according to claim 1 wherein from about 2 to about 5 moles lithium salt added per mole of dihydroxy prostaglandin alcohol.

3. The process according to claim 1 wherein the metal salt complex is formed at a temperature of about 0° to about 100° C.

4. The process according to claim 3 wherein the metal salt complex is formed at a temperature of about 20° to about 30° C.

5. The process according to claim 1 wherein the complex is decomposed by adding from about 10 to about 100 moles of water or $C_1$ to $C_3$ alcohol per mole of complex.

6. The process according to claim 1 wherein the alcohol is (±)-methyl 11,α,16-dihydroxy-16-methyl-9-oxoprost-4Z, 13E-diene-1-oate.

7. The process according to claim 1 wherein the alcohol is (±)-methyl 11α,16-dihydroxy-16-methyl-9-oxoprost-13E-en-1-oate.

* * * * *